(12) United States Patent
Silvian

(10) Patent No.: US 6,301,504 B1
(45) Date of Patent: Oct. 9, 2001

(54) HIGH SPEED TELEMETRY SYSTEM USING TRANSMISSION MEDIUM AS A COMPONENT OF A TELEMETRY LINK

(75) Inventor: Sergiu Silvian, La Crescenta, CA (US)

(73) Assignee: Pacesetter, Inc., Sylmar, CA (US)

( * ) Notice: Subject to any disclaimer, the term of this patent is extended or adjusted under 35 U.S.C. 154(b) by 0 days.

(21) Appl. No.: 09/415,480

(22) Filed: Oct. 8, 1999

(51) Int. Cl.[7] .................................................. A61N 1/37
(52) U.S. Cl. .................................................. 607/60
(58) Field of Search ................................ 607/9, 60, 32; 128/903; 455/95, 296, 899

(56) References Cited

U.S. PATENT DOCUMENTS

| | | | |
|---|---|---|---|
| 4,223,679 | 9/1980 | Schulman et al. | 128/419 |
| 4,681,111 | 7/1987 | Silvian | 128/419 PT |
| 4,712,555 | 12/1987 | Thornander et al. | 128/419 |
| 4,788,980 | 12/1988 | Mann et al. | 128/419 |
| 4,809,697 | 3/1989 | Causey, III et al. | 128/419 |
| 4,847,617 | 7/1989 | Silvian | 340/870.16 |
| 4,944,298 | 7/1990 | Sholder | 128/419 |
| 4,944,299 | 7/1990 | Silvian | 128/419 PG |
| 5,058,581 | 10/1991 | Silvian | 128/419 PG |
| 5,562,713 | 10/1996 | Silvian | 607/32 |
| 5,769,876 | 6/1998 | Silvian | 607/60 |

Primary Examiner—Scott M. Getzow

(57) ABSTRACT

The telemetry system allows a high speed transfer of digital data at for example 81,920 KHz, by utilizing the titanium can as a component of a telemetry link. The telemetry system includes a transmitter and a receiver that are interconnected by means of the telemetry link. Input data is fed to the transmitter where it is encoded, modulated, and transmitted through the can to the receiver. The can introduces a desired low pass filtering function that complements the signal encoding and modulation process implemented by the transmitter. The transmitter processes a binary data signal provided in Non-Return-to-Zero (NRZ) format. By a series of transformations, the transmitter produces a signal whose spectral properties closely match the telemetry link, including the titanium can. The titanium can becomes a source of controlled inter-symbol-interference (ISI) to be compensated for in the receiver.

23 Claims, 9 Drawing Sheets

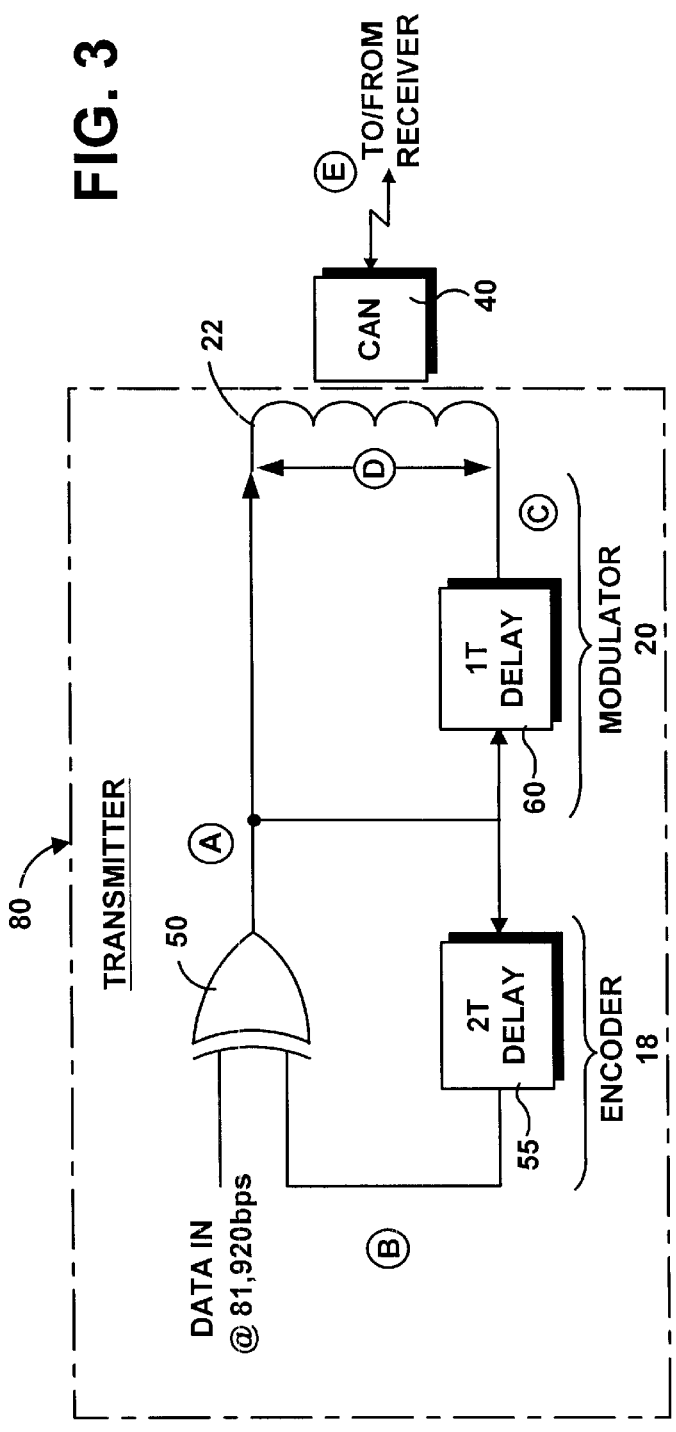
FIG. 3
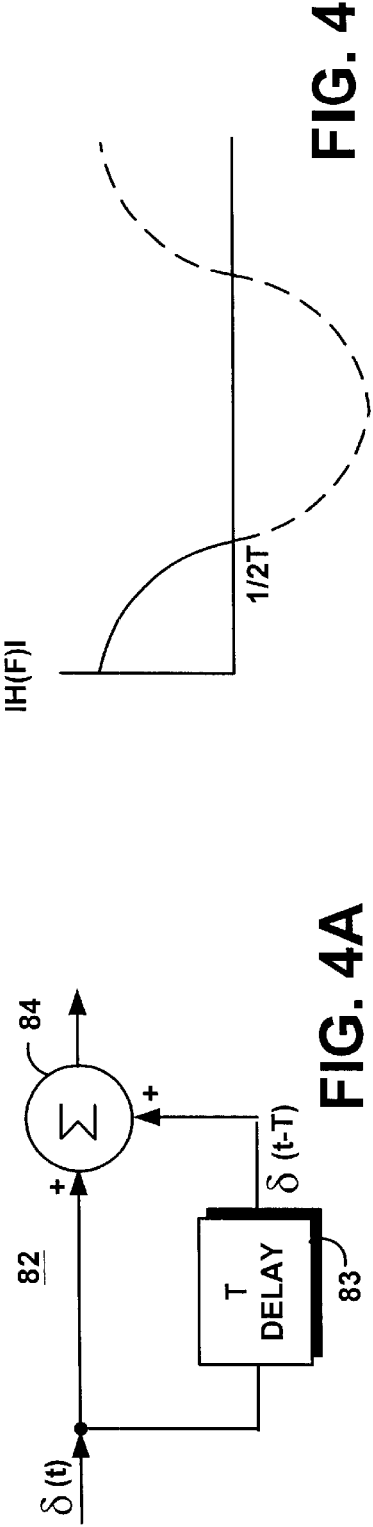
FIG. 4
FIG. 4A

HIGH SPEED TELEMETRY SYSTEM USING TRANSMISSION MEDIUM AS A COMPONENT OF A TELEMETRY LINK

FIELD OF THE INVENTION

The present invention relates generally to cardiac pacemakers, and other types of implantable medical devices that can be programmed and/or analyzed following implantation using an external diagnostic/programmer system. Particularly, the invention relates to a high speed digital telemetry system for use in implantable devices. More specifically, the present invention relates to an implantable high bit rate telemetry transmitter and corresponding external receiver that utilize the transmission medium as a component of the telemetry link

BACKGROUND OF THE INVENTION

Implantable devices are implanted in a human or animal for the purpose of performing a desired function. This function may be purely observational or experimental in nature, such as monitoring certain body functions; or it may be therapeutic or regulatory in nature, such as providing critical electrical stimulation pulses to certain body tissue, nerves or organs for the purpose of causing a desired response. Implantable medical devices such as pacemakers, perform both observational and regulatory functions, i.e., they monitor the heart to ensure it beats at appropriate intervals; and if not, they cause an electrical stimulation pulse to be delivered to the heart in an attempt to force the heart to beat at an appropriate rate.

In order for an implantable device to perform its functions at minimum inconvenience and risk to the person or animal within whom it is used, some sort of noninvasive telemetry means must be provided that allows data and commands to be easily passed back and forth between the implantable device and an external device. Such an external device, known by a variety of names, such as a controller, programmer, or monitor, provides a convenient mechanism through which the operation of the implantable device can be controlled and monitored, and through which data sensed or detected by the implantable device can be transferred out of the implantable device to an external (non-implanted) location where it can be read, interpreted, or otherwise used in a constructive manner.

As the sophistication and complexity of implantable devices has increased in recent years, the amount of data that must be transferred between an implantable device and its accompanying external device or programmer, has dramatically increased. This, in turn, has resulted in a search for more efficient ways to effectuate such a data transfer at high speed. The telemetry must not only transfer the desired data without significant error, but it must do so at a high speed while preserving the limited power resources of the implanted device.

Currently, three basic techniques have been used for communicating with an implantable device: (1) static magnetic field coupling; (2) reflected impedance coupling; and (3) RF coupling. In static magnetic field coupling, a static magnetic field is generated externally to the implanted device by using a permanent magnet, having sufficient strength to close (or open) a magnetic reed switch within the implanted device. While such a technique provides a fairly reliable mechanism for turning various functions within the implanted device ON or OFF, such as turning the telemetry circuits within an implanted device ON only when an external telemetry head is positioned a few inches from the implanted device, the technique is much too slow for efficiently transferring any significant amount of data. Further, for all practical purposes, the static magnetic system is mainly useful for transferring commands or data to the implanted device, not for transferring data or commands from the implanted device. This is because the weight and/or power requirements associated with the types of permanent magnets or electromagnets needed to operate a magnetic reed switch several inches distant therefrom is incompatible with the requirements of most implantable devices.

In a reflected impedance coupling system, information is transferred using the reflected impedance of an internal (implanted) L-R or L-C circuit energized by an inductively coupled, external L-R or L-C circuit. Such a system is shown, for example, in U.S. Pat. No. 4,223,679. While such a system uses little or no current to transmit information, the speed at which the information is transferred is quite limited. The external circuit uses an RF (radio frequency) magnetic field carrier. In the cited patent, a voltage controlled oscillator (VCO), in the implanted device, is controlled by the signal to be telemetered. The VCO, in turn, varies the impedance that is reflected. If the signal controlling the VCO is a binary digital signal (having two possible values, e.g., a binary "1" and a binary "0"), this signal encodes the VCO so that the VCO varies from one frequency (representing a binary "1") to another frequency (representing a binary "0"). This technique is known as frequency shift keying (FSK). Each bit duration, i.e., the time in which the binary digit (bit) is expressed, requires a number of carrier cycles. Hence, the bit rate cannot generally be much higher than 10% to 30% of the VCO center frequency. On the other hand, the RF carrier frequency cannot be too high because of the metal enclosure of the implanted device acts as a low pass, single pole filter having an upper cut-off frequency of between 10–30 kHz. Further, the external oscillator L-C circuit typically has a Q (quality factor) of 20 to 50, meaning that the useful modulation bandwidth is limited to around 2 to 5 percent of the RF carrier frequency. This means that a 36 kHz carrier is typically only able to transmit data at a data rate of from 72 to 540 bits per second (bps). Such a rate is generally considered inadequate for modern implantable devices, which devices may have thousands of bits of data to be transmitted.

In an RF coupled system, information is transferred from a transmitting coil to a receiving coil by way of a carrier signal. The carrier signal is modulated with the data that is to be transmitted using an appropriate modulation scheme, such as FSK or PSK (phase-shift keying for reversing the phase of the carrier by 180 degrees). The modulated carrier induces a voltage at the receiving coil that tracks the modulated carrier signal. This received signal is then demodulated in order to recover the transmitted data. Because of the metal enclosure of the implanted device, which acts as a low pass filter (attenuating high frequencies), the carrier frequency cannot be increased above approximately 10–20 kHz without an unacceptable increase in transmitting coil power. Further, depending upon the type of modulation/demodulation scheme employed, the data or bit rate cannot exceed a prescribed fraction of the carrier frequency, without exceeding a specified amount of mutual interference, i.e., without being able to reliably distinguish between a modulation that represents a binary "1" and modulation that represents a binary "0".

The maximum data transfer rate (bit rate) at which independent signal values can be transmitted over a specified channel without exceeding a specified amount of mutual interference is referred to as the "Nyquist rate." The maximum allowable Nyquist rate is directly related to the bandwidth of the channel through which the data is transferred. Conversely, the "Nyquist bandwidth" is that bandwidth required to allow independent signal values to be transmitted at a given rate without exceeding the specified levels of mutual interference. For example, if the bandwidth of the channel through which the data is transferred is W, the Nyquist rate (assuming an ideal channel) may be as high as 2W. Stated differently, if the data rate is 2W, the Nyquist bandwidth must be at least W. Because of these and other limitations, conventional implantable devices using RF coupling have generally not been able to transfer data at rates in excess of 2–4 kbps. It should be noted that a one-sided bandwidth definition is used, namely that a bandwidth W refers to a range of frequencies from 0 to W, or from −W to 0. Where a carrier signal having a frequency $f_c$ is used, the one-sided bandwidth W refers to a range of frequencies from $f_c$ to $(f_c+W)$, or from $(f_c-W)$ to $f_c$.

A further problem affecting the rate at which data can be transferred from an implantable device is electrical noise and/or EMI (electromagnetic interference). In particular, there are at least two primary sources of EMI associated with commonly used types of external devices that significantly affect the range of carrier frequencies and data rates that can be reliably and efficiently (at low power consumption levels) used to transfer data in an RF-type system. First, the input power line frequency (50–60 Hz) of the external device, and the associated switching magnetic fields (e.g., 30 Hz) used with a cathode ray tube (CRT) display, frequently used with external devices, create sufficiently large EMI harmonics to be troublesome as high as 2–6 kHz. Similarly, the 16 kHz line frequency of the horizontal scan of the cathode ray tube (CRT) commonly used with many electronic terminals, makes it extremely difficult to efficiently use a carrier frequency of 16 kHz or higher. In order to minimize the effect of such EMI on the transmission of data from an implanted device used in an environment where such interference is prevalent, and in order to maximize the speed at which the large amounts of data used with modern implantable devices may be transferred, it would be preferable to employ a narrow band telemetry channel to filter out as much EMI and noise as possible using a carrier signal in the 6–12 kHz range, and using a modulation scheme that permits a data bit rate as high as possible through such channel.

A telemetry system that addresses this problems and that presents a solution to allow data to be transferred at an acceptably fast rate, e.g., 8 kHz, and to also allow the data at this fast rate to be transferred through a narrow bandwidth, thereby decreasing the susceptibility of the system to EMI and other noise sources is described in U.S. Pat. No. 4,944,299 to Silvian.

An additional problem present facing conventional telemetry systems is the presence of the titanium can along the telemetry link. Heretofore, this problem remains unsolved. The reason for considering the titanium can to be highly undesirable is that the titanium limits the bandwidth of the channel by attenuating the high frequencies in a manner similar to that of a low pass filter. In particular, the higher frequencies are attenuated as by a low pass filter with a −3 dB frequency of 10–15 KHz. In the current state of the art, this attenuation of higher frequencies causes increasing inter-symbol-interference (ISI) as the data rate approaches the cutoff frequency. The ISI, in turn, causes distortion of the received signal which degrades performance, limits the maximum data rate, or renders reliable reception impossible.

Therefore, there is a great, and still unsatisfied, need for a telemetry system that overcomes the problem associated with the presence of the titanium can, and that allows for a high data transfer of information particularly from the implantable device to the external programmer.

SUMMARY OF THE INVENTION

The present invention addresses these and other concerns by providing an improved telemetry system. According to a preferred embodiment, the telemetry system allows a high speed transfer of digital data at for example 81,920 KHz, and further utilizes the transmission medium, such as the titanium can as a component of the telemetry link.

The telemetry system accomplishes this goal without including added new components, and without significantly increasing the overall cost of the implanted device.

The foregoing and other features of the present invention are achieved by a telemetry system that includes a transmitter and a receiver that are interconnected by means of a telemetry link. The transmitter is generally comprised of a data encoder, a modulator, and a transmit coil. The receiver is generally comprised of a receive coil, an amplifier, a band-pass filter, and a demodulator. The telemetry link maintains data communication between the transmitter and the receiver 14, and includes the transmit coil, the receive coil, and a part of a titanium can that houses the transmitter.

Input data is fed to the transmitter where it is encoded by the encoder, modulated by the modulator, and transmitted by the transmit coil, through the can, to the receiver. The can introduces a desired low pass filtering function, which complements the signal encoding and modulation process implemented by the transmitter. The signal transmitted over the telemetry link is received by the receive coil, amplified by the amplifier, filtered by the band-pass filter, and demodulated by the demodulator.

The telemetry system can transmit data at a high rate, for example 81,920 Hz. The transmitter processes a binary data signal provided in Non-Return-to-Zero (NRZ) format. By a series of transformations, the transmitter produces a signal whose spectral properties closely match the telemetry link, including the titanium can. Data rates in excess of those possible with the current state of the art are supported by including the spectral properties of the titanium can in the transfer function for the whole telemetry system. In effect, the titanium can becomes a source of controlled inter-symbol-interference (ISI), to be compensated for in the receiver.

The presence of the titanium can in the telemetry link is desirable in that it becomes part of the encoding process, and overcomes the bandwidth limitations. The telemetry system employs a partial response signaling which is combined with the low pass filter characteristic of the titanium can.

The particular channel response employed in the telemetry system 10 is termed a $(1-D^2)$ channel, where 'D' is the delay operator and represents one bit time. The overall $(1-D^2)$ characteristic can be obtained by multiplying an input signal by $(1-D)$ and $(1+D)$ in succession. This channel response is implemented by using the low pass filter characteristic $(1+D)$ of the titanium can, which is preceded by a $(1-D)$ function in the modulator. The combined behavior of $(1+D)*(1-D)$ produces the desired channel spectrum.

DESCRIPTION OF THE DRAWINGS

The various features of the present invention and the manner of attaining them will be described in greater detail with reference to the following description, claims, and drawings, wherein reference numerals are reused, where appropriate, to indicate a correspondence between the referenced items.

FIG. 3 is a more detailed circuit diagram of the transmitter of FIG. 1, according to a second embodiment of the present invention.

FIG. 4 is a frequency response diagram illustrating a desired low pass filter channel frequency response function which is similar to the attenuation introduced by a can that forms part of the telemetry link of FIG. 1.

FIG. 4A is a diagram of a circuit that provides a (1+D) frequency response shown in FIG. 4, as implemented by the can.

DETAILED DESCRIPTION OF THE PREFERRED EMBODIMENTS

Figure 1:
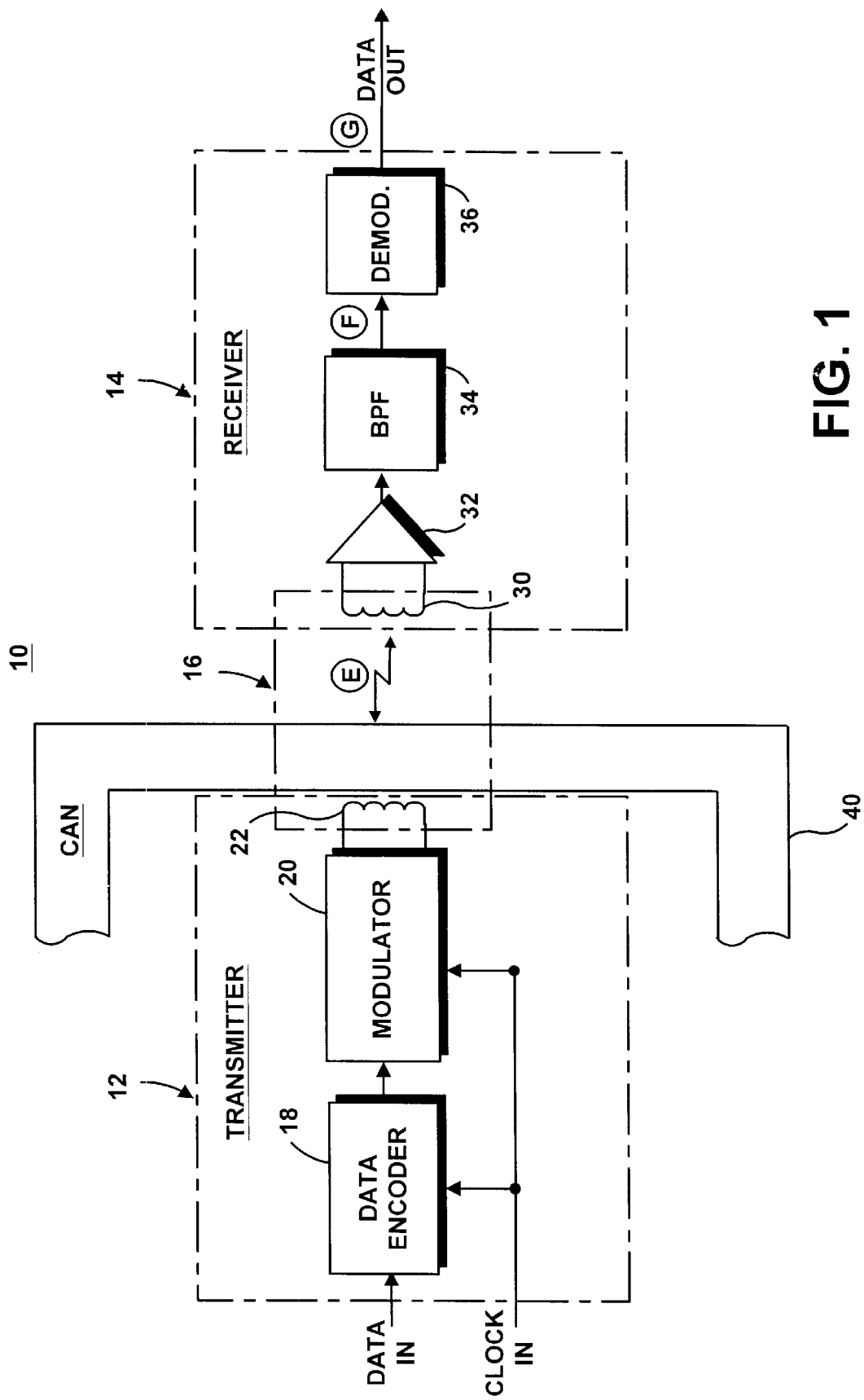
FIG. 1 is a high level schematic diagram of a telemetry system of the present invention comprised of a transmitter and a receiver that are interconnected by means of a telemetry link.

FIG. 1 illustrates a telemetry system 10 according to the present invention. The telemetry system 10 includes a transmitter 12 and a receiver 14 that are interconnected by means of a telemetry link 16. The transmitter 12 is generally comprised of a data encoder 18, a modulator 20, and a transmit coil 22. The receiver 14 is generally comprised of a receive coil 30, an amplifier 32, a band-pass filter 34, and a demodulator 36. The telemetry link 16 maintains data communication between the transmitter 12 and the receiver 14. The telemetry link 16 includes the transmit coil 22, the receive coil 30, and a part of a titanium can 40 that houses the transmitter 12. The titanium can 40 will also be referred to herein as housing 40.

Input data (DATA IN) is fed to the transmitter 12 where it is encoded by the encoder 18, modulated by the modulator 20, and transmitted by the transmit coil 22, through the can 40, to the receiver 14. The can 40 introduces a desired low pass filtering function, which complements the signal encoding and modulation process implemented by the transmitter 12. The signal transmitted over the telemetry link 16 is received by the receive coil 30, amplified by the amplifier 32, filtered by the band-pass filter 34, and demodulated by the demodulator 36.

The telemetry system 10 can transmit data at a high rate, for example 81,920 Hz. The transmitter 12 processes a binary data signal provided in Non-Return-to-Zero (NRZ) format, although any other suitable binary format may be used. NRZ signals consist of two levels, with a first level corresponding to a binary "1" and a second level corresponding to a binary "0". By a series of transformations explained more fully below, the transmitter 12 produces a signal whose spectral properties closely match the telemetry link 16, including the titanium can 40. Data rates in excess of those possible with the current state of the art are supported by including the spectral properties of the titanium can 40 in the transfer function for the whole telemetry system 10. In effect, the titanium can 40 becomes a source of controlled inter-symbol-interference (ISI) to be compensated for in the receiver 14, as it will be explained later in greater detail.

The presence of the titanium can 40 in the telemetry link 16 is desirable in that it becomes part of the encoding process, and overcomes the bandwidth limitations. The telemetry system employs a partial response signaling which is combined with the low pass filter characteristic of the titanium can 40.

Partial response channels, which employ partial response signaling, allow controlled ISI by incorporating the effects of adjacent symbol interactions into the encoding and decoding process. For example, if it is known that a portion of an adjacent symbol will spread over into the current symbol space, it is possible to subtract this effect at the receiver end. The telemetry system 10 takes advantage of the partial response signaling feature which is offered by the titanium can 40 and which is incorporated into the overall transfer function of the telemetry system 10.

The particular channel response employed in the telemetry system 10 is termed a $(1-D^2)$ channel, where 'D' is the delay operator and represents one bit time. The overall $(1-D^2)$ characteristic can be obtained by multiplying an input signal by $(1-D)$ and $(1+D)$ in succession. This channel response is implemented by using the low pass filter characteristic $(1+D)$ of the titanium can 40, which is preceded by a $(1-D)$ function in the modulator 20. The combined behavior of $(1+D)*(1-D)$ produces the desired channel spectrum.

With reference to FIG. 1, the data encoder 18 divides the binary input signal (DATA IN) by $(1-D^2)$ to simplify the decoding, by the receiver 14, of the signal that has been processed by the transmitter 12 and the can 40. Simplification occurs because the combined effect of the encoder (i.e., division by $1-D^2$), and the rest of the channel (multiplication by $1-D^2$), results in a signal at the receiver 14, which after suitable equalization, closely resembles the original input signal. That is, the transfer function of the telemetry system 10 between the original data source and the receiver 14 is unity or close to unity.

The modulator 20 modifies the signal encoded by the encoder 18 by multiplying it with a $(1-D)$ factor in preparation for transmission through the telemetry link 16. The transmit coil 22 has a ferrite core with low impedance, to support higher transmission rates in accordance with the present invention. For illustration purpose only, the coil 22 is used for a 81,920 bps transmission rate.

As used herein, a transmission medium includes any material in the telemetry link 16, which conducts the signal between the transmit coil 22 and the receive coil 30. This includes portions of the body in which the device is implanted, air, and the titanium can 40. Optionally, the transmission medium can include any material or component used by the receiver 14 to change the reception characteristic of the received signal.

According to the present invention, the treatment of the titanium can 40 as a component of the telemetry link 16 allows the telemetry link 16 to operate at considerably higher data rates by combining the filtering characteristic (or spectral response) of the can 40 with the particular partial response function chosen. While in a conventional telemetry system the presence of the titanium can imposes a bandwidth limitation on higher data rates because it produces distortion associated with ISI, in the present invention, however, the combination of the spectral response of the titanium can 40 with the modulator function satisfies the partial response requirements for the overall channel which is designed to operate properly with controlled ISI.

Figure 2:
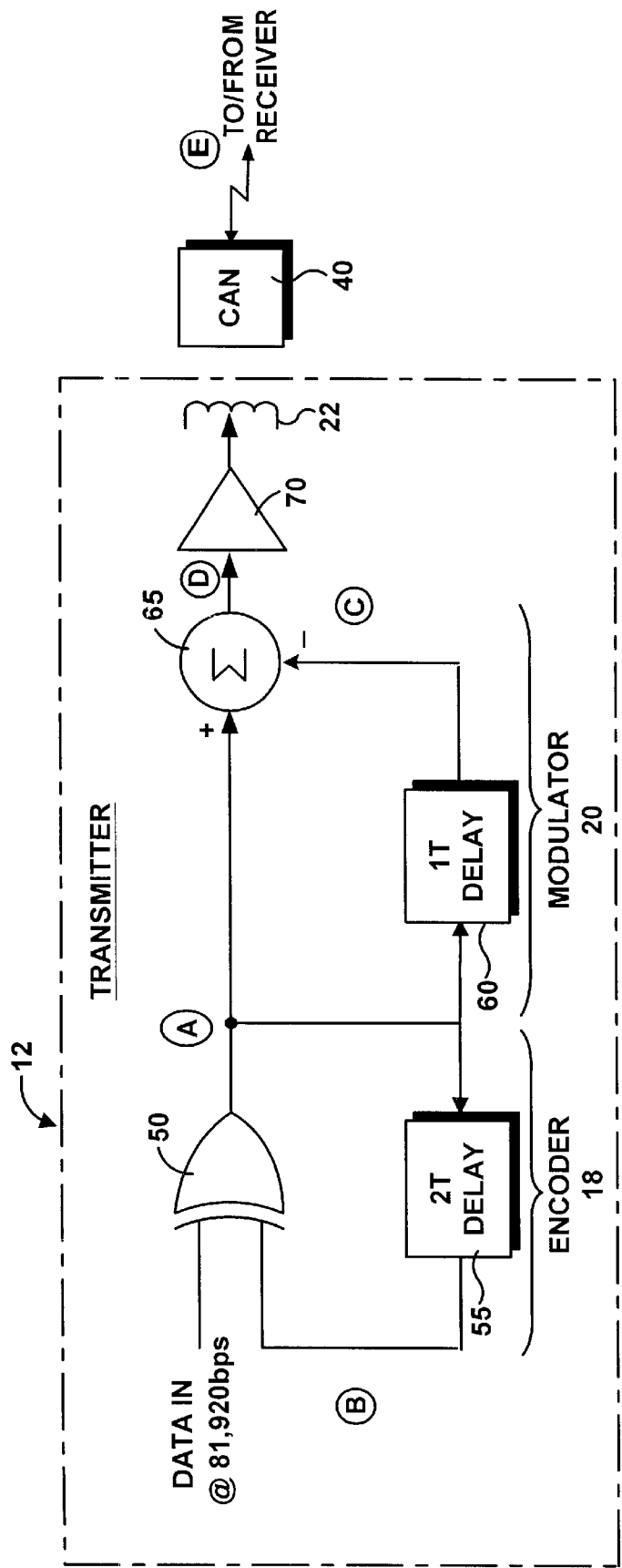
FIG. 2 is a more detailed circuit diagram of the transmitter of FIG. 1, according to a first embodiment of the present invention.

FIG. 2 illustrates an exemplary implementation of the transmitter 12 according the present invention. In this embodiment, the encoder 18 is comprised of a logic gate 50, such as an exclusive OR, which is connected at one of its inputs to the input data. The output of the logic gate 50 is fed to a 2T-delay circuit 55, for introducing a delay of 2T, and therefrom to the other input of the logic gate 50. As used herein, T refers to the period of the data rate, for example 1/81,920 Hz.

The modulator 20 is comprised of 1T-delay circuit 60 that introduces a delay of T to the signal at the output of the encoder 18, and that feeds the delayed signal to the negative terminal of a summer (or a summation circuit) 65 configured as a subtractor. The output of the encoder 18 is fed to the positive terminal of the summer 65. The overall effect of the modulator 20 is to provide the desired (1−D) response function. The signal at the output of the summer 65 is amplified by an amplifier 70, and is transmitted over the telemetry link 16 via the transmit coil 22.

As explained above, the inclusion of the titanium can 40 as a component of the telemetry link 16 adds a desired low pass filter characteristic whose spatial spectrum is illustrated in FIG. 4, and which is closely approximated by a (1+D) response function. This response function can also be represented mathematically by the following equation (1):

$$h(t)=\delta(t)+\delta(t-T), \quad (1)$$

where h(t) is the response function in FIG. 4, $\delta(t)$ is the data bit at time t, and $\delta(t-T)$ is the data bit at time (t−T).

Equation (1) can be expressed in the frequency domain by the following equations (2) and (3):

$$H(f)=1+e^{-j2\pi fT} \quad (2)$$

$$|H(f)|=2\cos\pi fT \quad (3)$$

It can be seen that the cosine function of equation 3 can be represented by the graph of FIG. 4.

FIG. 4A is a diagram of a circuit 82 that provides an equivalent (1+D) function to that provided by the can 40, and approximated by the cosine function of FIG. 4. The circuit 82 includes a 1T-delay circuit 83 and a summer 84. The summer 84 adds the data bit $\delta(t)$ at time t and the data bit $\delta(t-T)$ at time (t−T), to generate the response function h(t) expressed by equation (1) above.

Figure 5:
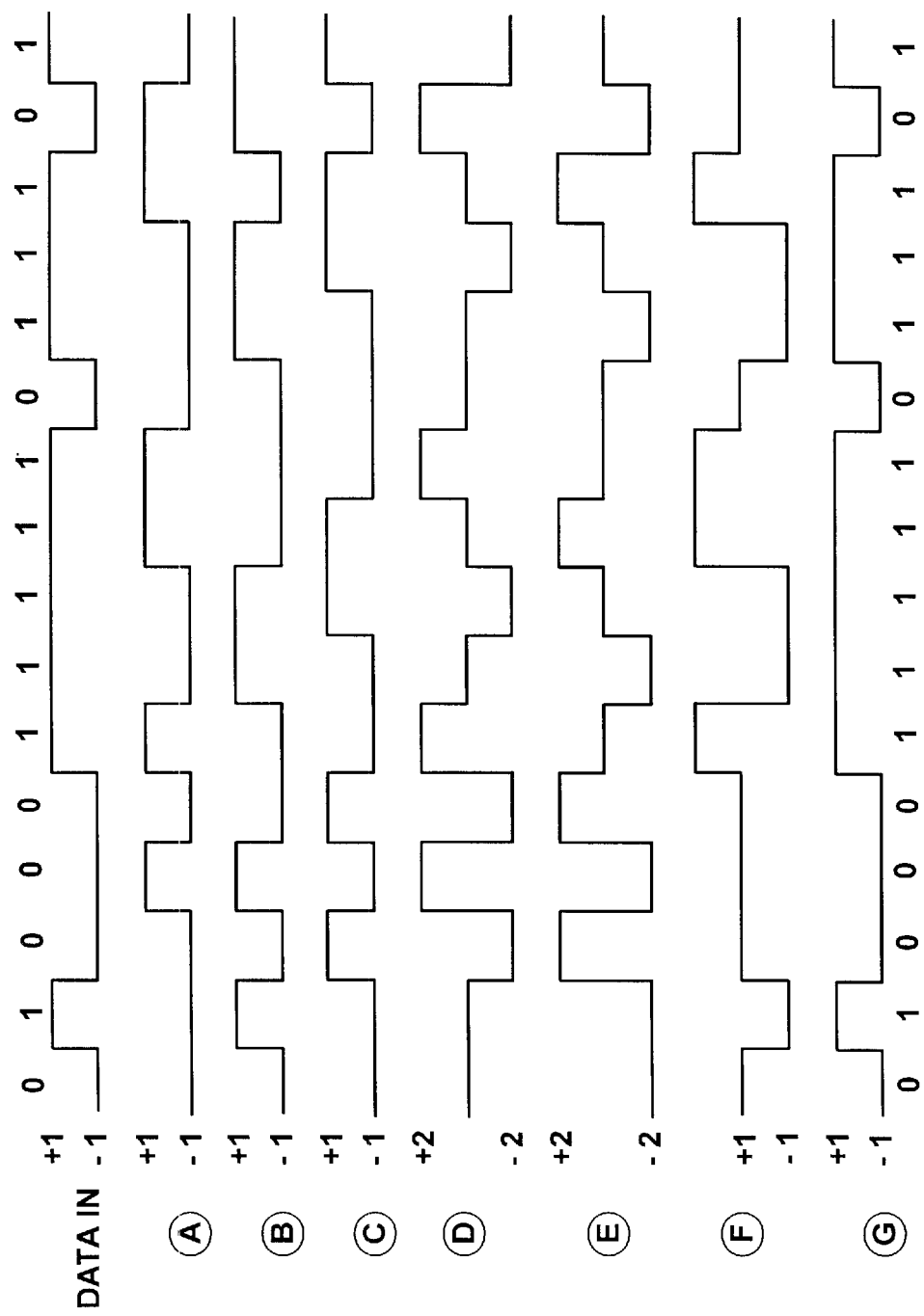
FIG. 5 is an exemplary timing diagram illustrating the encoding, modulation, and decoding process as implemented by the telemetry system of FIG. 1.

FIG. 5 illustrates the operation of the telemetry system 10 by considering an exemplary data string (DATA IN), and by tracking its transformation along various points. The input data string (DATA IN) is a string of binary or digital data that switches between two levels +1 and −1 representing a binary "1" or binary "0", respectively.

The encoder 18 (FIG. 2) divides the DATA IN by (1−$D^2$). The encoder output at point A is the mod 2 addition of the DATA IN, and the signal at point B is the encoder output delayed by two clocks cycles. The operation of the encoder 18 on the DATA IN assures that the signal output at point A is the original DATA IN divided by (1−$D^2$).

The modulator 20 receives its input from the encoder 18 and generates a (1−D) function which is applied to the input signal. The signal at point C, is a one clock cycle-delayed version of the signal at point A. The signal at point D is the result of subtracting the signal at point C from the signal at point A, and is a three-level signal where "short steps", e.g. "0" to "2", "0" to "−2", "2" to "0", or "−2" to "0" are to be interpreted as binary "1s" and "long steps", e.g. "−2" to "2" and "2" to "−2" represent binary "0s". The absence of any step also represents a binary "0".

The signal at point D is amplified by the amplifier 70 without changing its characteristics, and is thereafter transmitted at point E, via the transmit coil 22 and the can 40 to the receiver 14. The can 40 generates a (1+D) function which is applied to the signal at point D as amplified.

At the receiver 14, the signal at point E is amplified by the amplifier 32 without changing its characteristics, and is passed through the band-pass filter 34 that corrects for the (1+D) factor introduced by the can 40. The signal at the output of the band-pass filter 34, at point F, is demodulated by the demodulator 36 by multiplying it with a (1−$D^2$) factor. The signal at the output of the demodulator 36, at point F, becomes a substantial replicate of the input signals DATA IN.

The receive coil 30 is designed to pick up the signals produced by the transmit coil 22 (or coil 120 in FIG. 8) after those signals have passed through the can 40. The received signals are attenuated by the loosely coupled coils 22, 20 and by the can 40, and are amplified by the amplifier 32 to a level suitable for introduction into the band-pass filter 34.

In a partial response channel, the filter 34 normally serves two functions. The first function is the attenuation of high frequency noise which can otherwise produce errors in the receiver 14, and the second function is to equalize or "shape" the signal so that any distortion introduced by the telemetry link 16 are suppressed.

The properly equalized signal which is available at the output of the filter 34 is applied to the demodulator 36, whose role is to convert the input signal into a series of digital values. The receiver 14 generates a sequence of binary digital signals which represent the original, transmitted data (DATA IN).

The overall function of the telemetry system 10, in accordance with the present invention, is to transmit the binary signals originating in an implanted device to a suitable configured receiver 14 which restores the original binary signals. Having successfully recreated the original data at the remote receiver location, the data may then be further processed or interpreted, as desired.

FIG. 3 illustrates a transmitter 80 according to an alternative embodiment of the present invention. The transmitter 80 is generally similar in function and design to the transmitter 12 of FIG. 2. In the transmitter 80, the summation circuit 65, the amplifier 70 and the transmit coil 22 are replaced by a simpler design comprised of the transmit coil 22. It should be clear to a person of ordinary skill in the field that other transmitter designs are also operable with the present invention.

Figure 6:
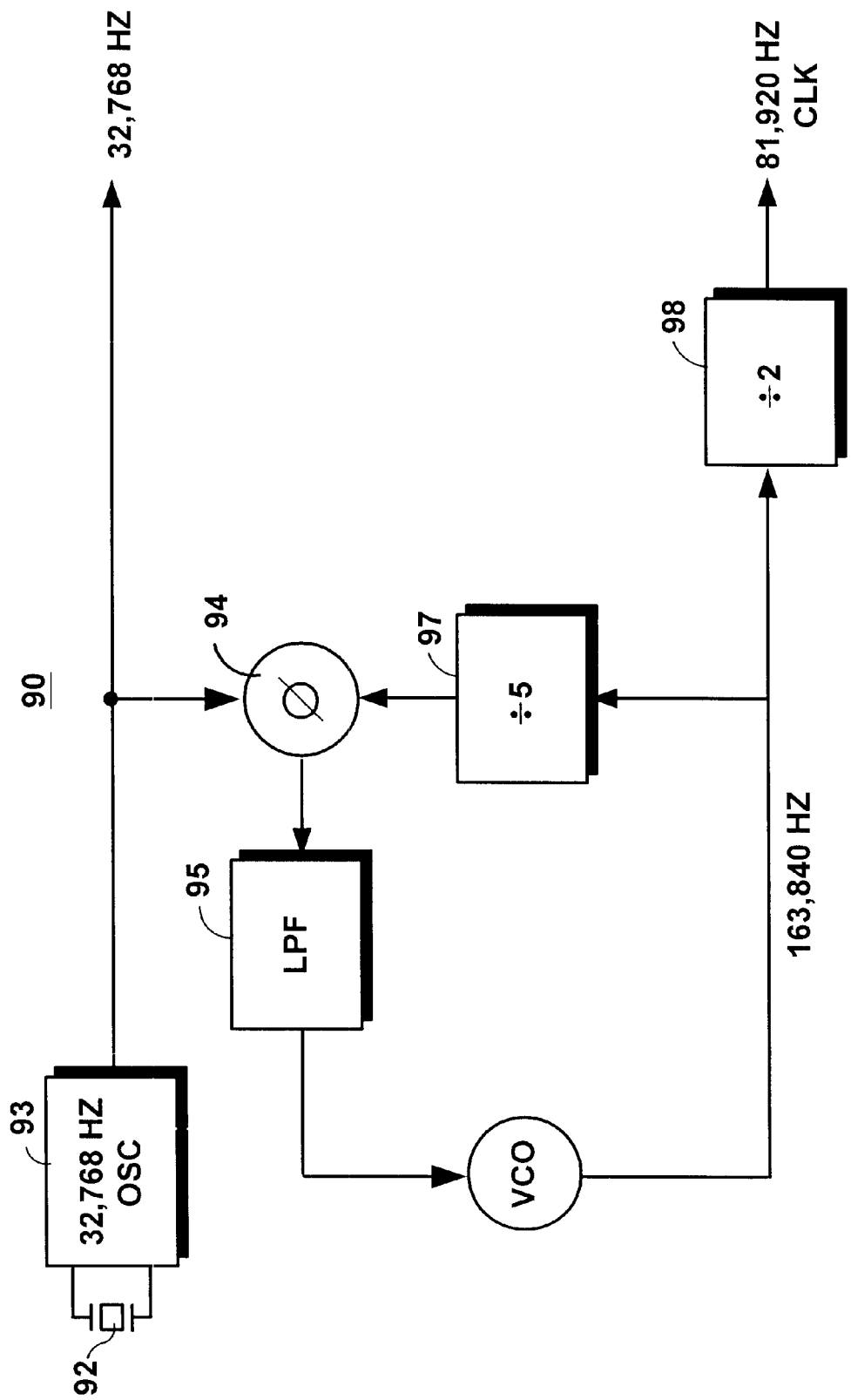
FIG. 6 is an exemplary circuit diagram of a clock generation circuit for providing the clock signals to the transmitter of FIG. 1.

FIG. 6 illustrates an exemplary clock generation circuit 90 that provides the clock signals to the transmitter 12 of FIG. 1. The clock generation circuit 90 provides a stable reference clock for the operation of the encoder 18, the modulator 20, and the transmit coil 22, to enable operation at 81,920 Hz, in accordance with the present invention. Timing reference signals at other frequencies are also provided. The clock generation circuit 90 takes into account the fact that most implantable devices already have a 32,768 Hz crystal-controlled oscillator.

The clock generation circuit 90 includes a crystal 92 connected across a 32,768 Hz oscillator 93. The output of the oscillator 93 is connected to a phase detector 94, which, in turn, is connected to a low pass filter 95. The output of the low pass filter 95 is connected to a voltage controlled oscillator (VCO) 96. The output of the VCO 86connected to the phase detector 94 via a divider 97, and to the input of the telemetry circuit 10 of FIG. 1, via a divider 98, in order to provide the desired 81,920 Hz clock signal to the telemetry circuit 10.

The telemetry system 10 of FIG. 1 requires a bandwidth of 40,960 Hz (½ 81,920 Hz), and has a peak distribution at 20,480 Hz, with no DC response. The current consumption of the telemetry system 10 may exceed the design expectations for a particular application, in which event a backup telemetry mode might be useful.

Figure 7:
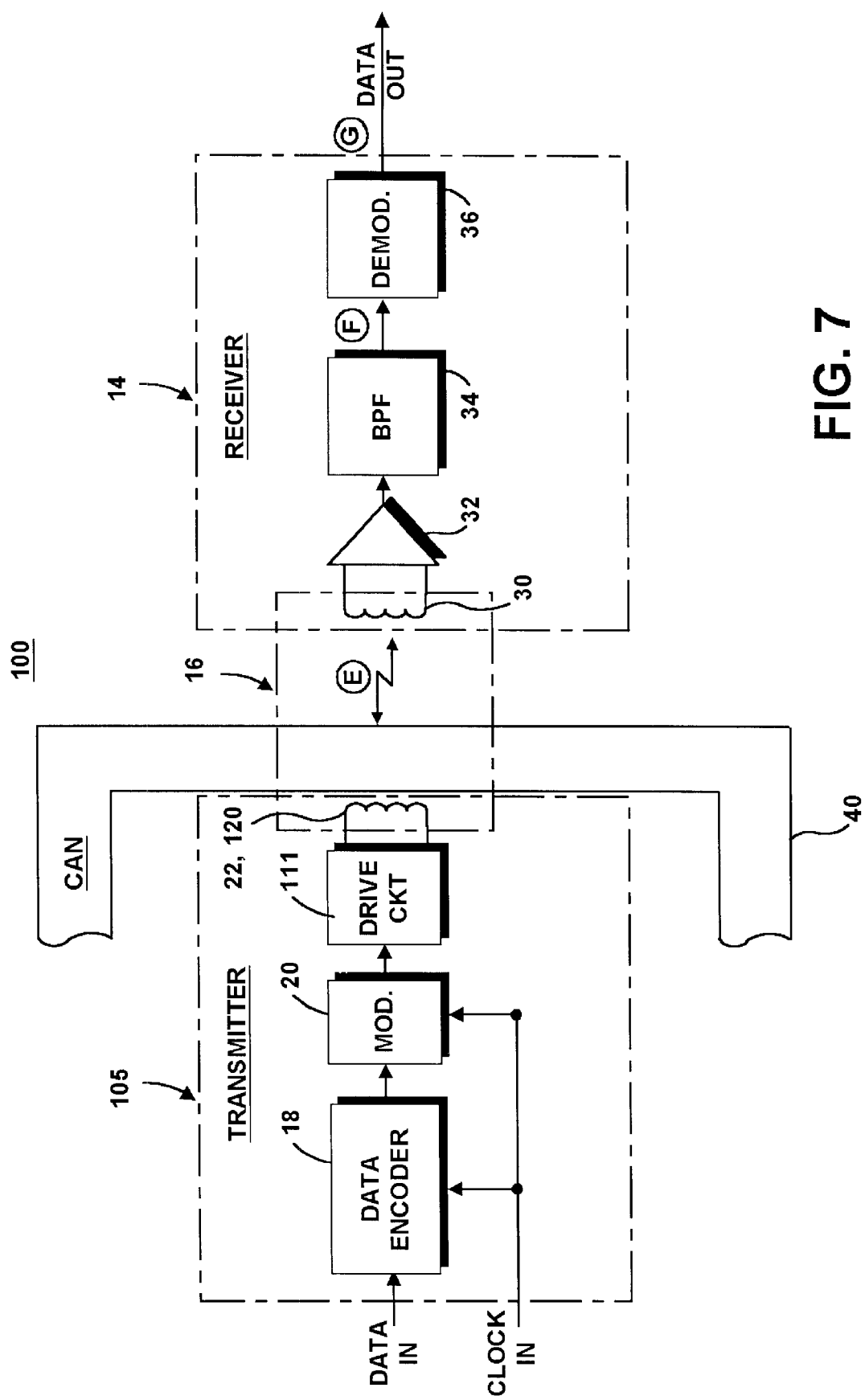
FIG. 7 is a high level schematic diagram of another telemetry system of the present invention comprised of a transmitter and a receiver that are interconnected by a telemetry link.
Figure 8:
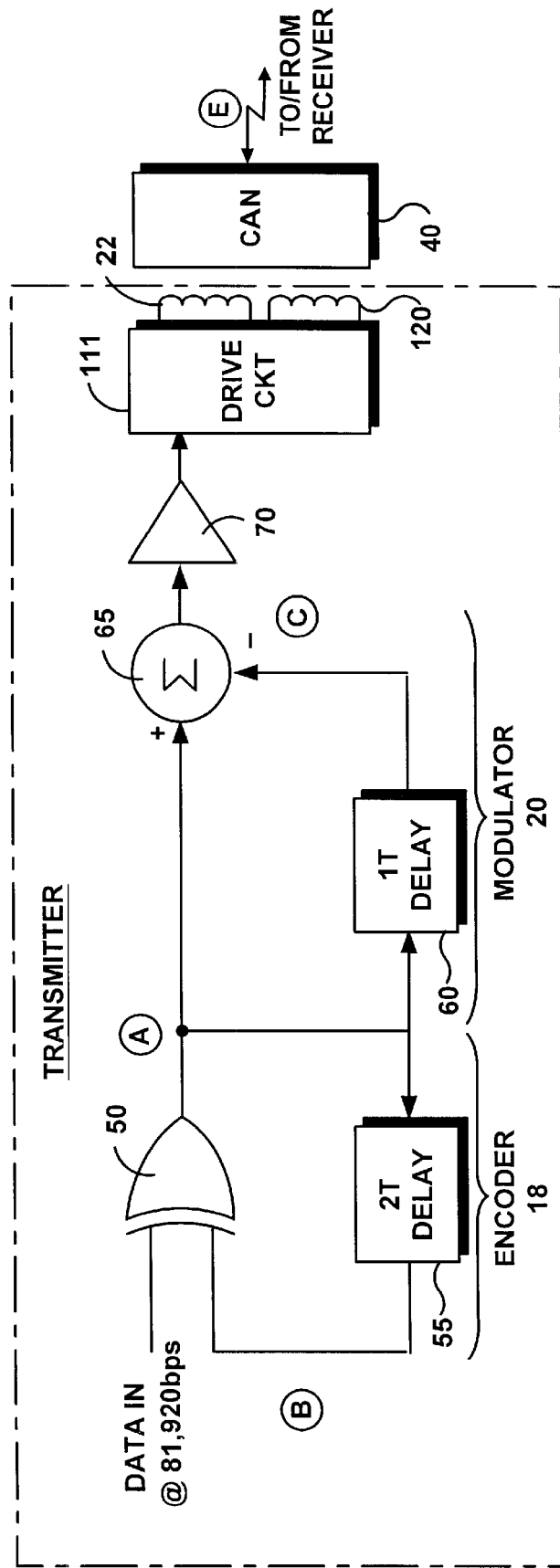
FIG. 8 is a more detailed circuit diagram of a portion of the transmitter of FIG. 7.

FIGS. 7 and 8 illustrate such a telemetry system 100 which is capable of transmitting data in one of two distinct modes: a high data rate mode operating at 81,920 Hz, and a lower data rate mode operating at 8,192 Hz. To accomplish this modal duality, the telemetry system 100 is provided with a transmitter 105 and a receiver 14. The receiver 14 is generally similar to that of the telemetry system 10.

The transmitter 105 is substantially similar to the transmitter 12 of the telemetry system 10 of FIGS. 1 and 2, but additionally includes a transmit coil drive circuit 111 and another coil 120. The transmit coil drive circuit 111 selects and drives one of the two coils 22, 120 to produce the signal which is coupled into the telemetry link 16. The selection of the coil 22, 120 is based on the requirement of the telemetry system 100 to transmit at the lower 8,192 bps data rate or at the higher 81,920 bps data rate.

As described above, the coil 22 has a ferrite core with low impedance, for supporting the higher transmission rates, such as 81,920 bps in accordance with the present invention. The coil 120 is used for transmission and reception of signals at lower transmission rates, such as 8,192 bps, and has a mumetal core and high impedance, to provide a low power transmission path for data at lower rates.

Figure 9:
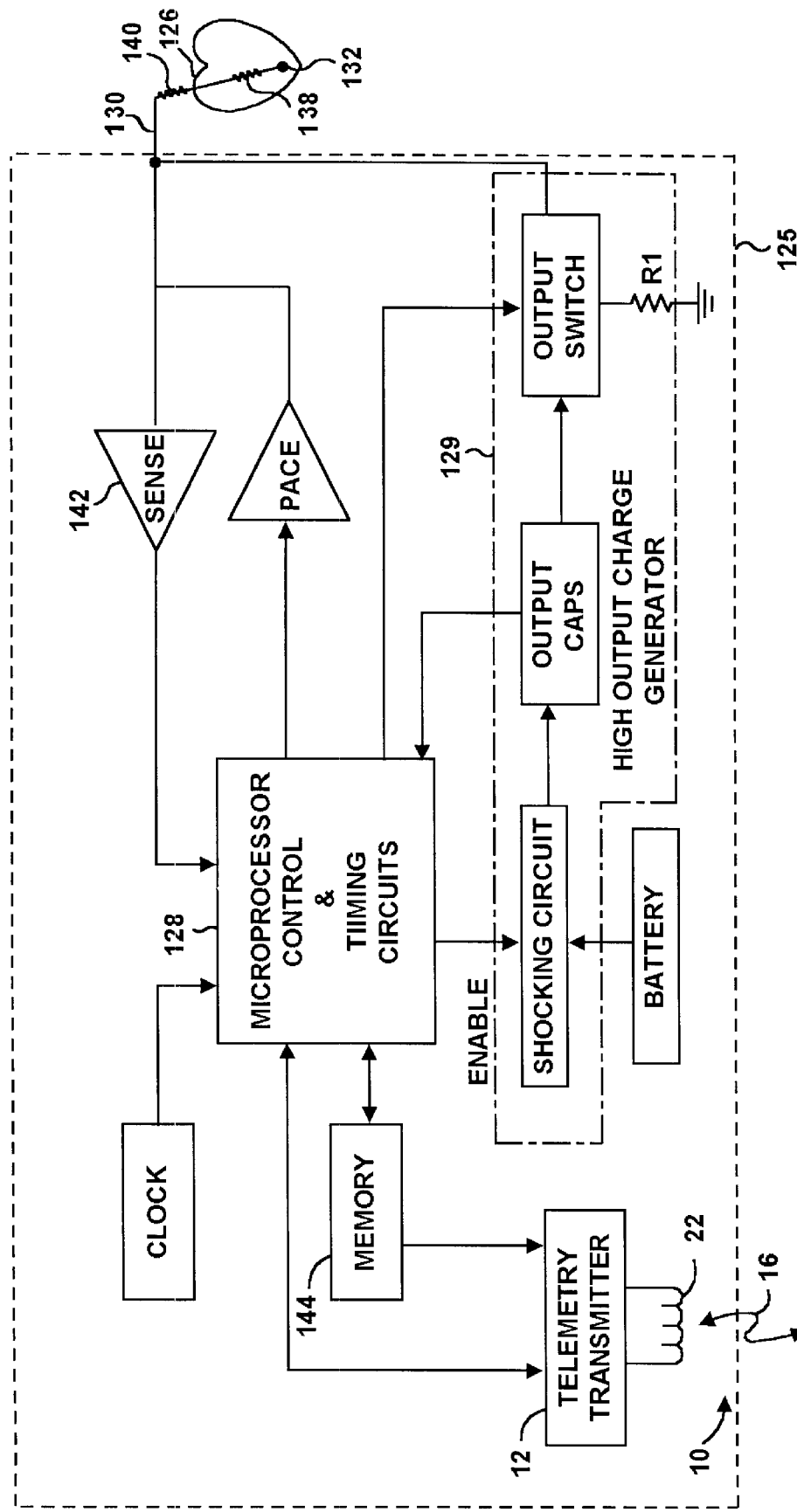
FIG. 9 is a functional block diagram of an implantable cardioverter defibrillator (ICD), which represents one type of implantable stimulation device with which the present invention may be used.
Figure 10:
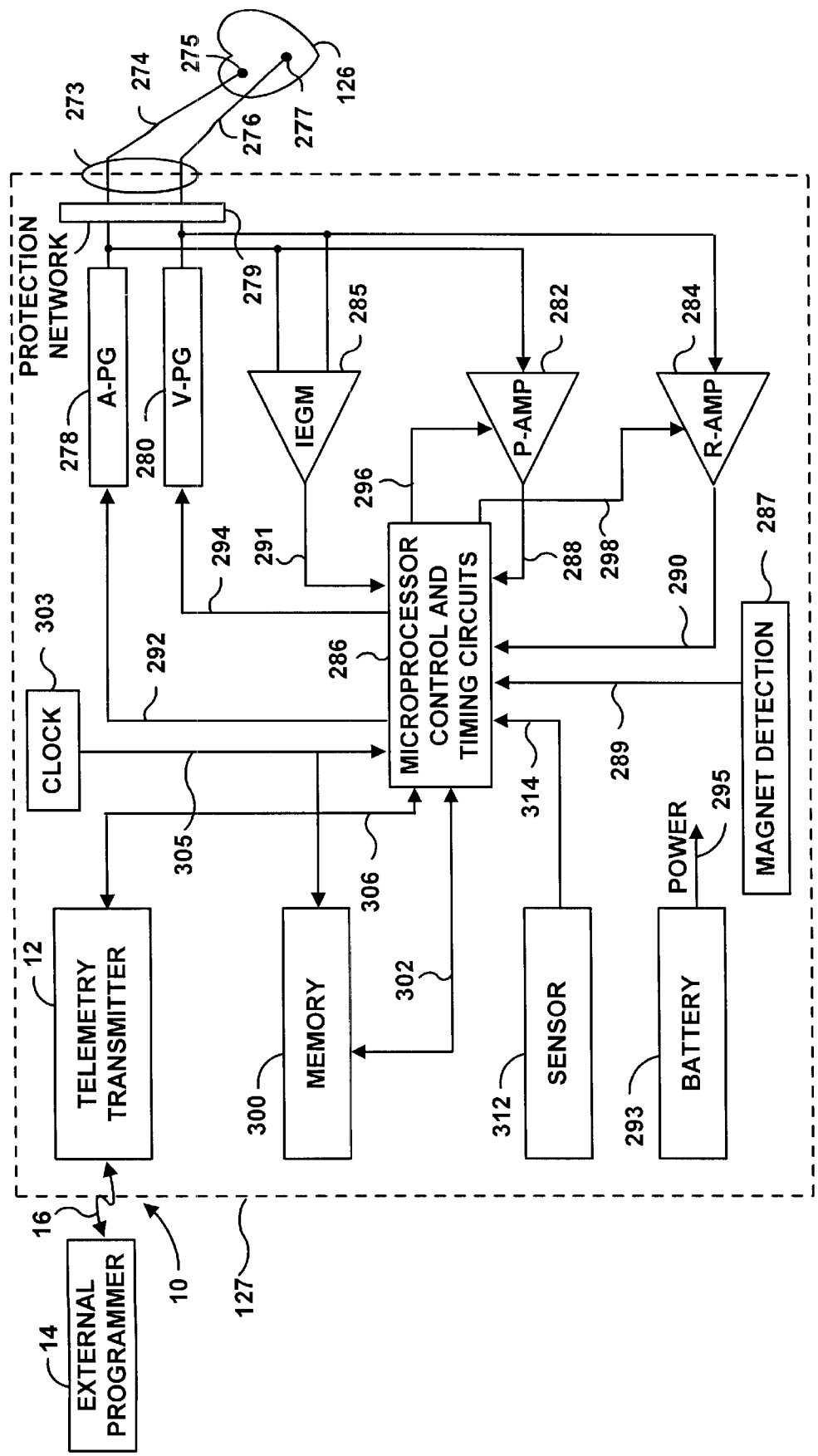
FIG. 10 is a functional block diagram of an implantable dual-chamber pacemaker, which represents another type of implantable medical device with which the invention may be used.

FIG. 9 shows a simplified functional block diagram of an ICD device 125, and FIG. 10 shows a simplified functional block diagram of a dual-chamber pacemaker 127, which incorporate the telemetry system 10 of the present invention. It should also be noted that in some instances the functions of an ICD and a pacemaker may be combined within the same stimulation device. However, for teaching purposes, the devices will be described as separate stimulation devices.

It is the primary function of an ICD device 125 to sense the occurrence of an arrhythmia, and to automatically apply an appropriate electrical shock therapy to the patient's heart 126 aimed at terminating the arrhythmia. To this end, the ICD device 125, as shown in the functional block diagram of FIG. 9, includes a control and timing circuit 128, such as a microprocessor, state-machine or other such control circuitry, that controls a high output charge generator (or pulse generator) 129. The high output charge generator 129 generates electrical stimulation pulses of moderate or high energy (corresponding to cardioversion or defibrillation pulses, respectively), e.g., electrical pulses having energies of from 1 to 10 joules (moderate) or 11 to 40 joules (high), as controlled by the control/timing circuit 128.

Such moderate or high energy pulses are applied to the patient's heart 126 through at least one lead 130 having at least two defibrillation electrodes, such as coil electrodes 138 and 140. The lead 130 preferably also includes at least one electrode for pacing and sensitivities, such as electrode 132. Typically, the lead 130 is transvenously inserted into the heart 126 so as to place the coil electrodes 138 and 140 in the apex of the heart 126 and in the superior vena cava, respectively. While only one lead 130 is shown in FIG. 9, it is to be understood that additional defibrillation leads and electrodes may be used as desired or needed in order to efficiently and effectively apply the shock treatment generated by the high voltage generator 129 to the patient's heart 126.

The ICD device 125 also includes a sense amplifier (or detection circuit) 142 that is coupled to at least one sensing electrode 132. It is the function of the sense amplifier 142 to sense the electrical activity of the heart 126, such as R-waves which occur upon the depolarization, and hence contraction, of ventricular tissue; and P-waves which occur upon the depolarization, and hence contraction, of atrial tissue. Thus, by sensing R-waves and/or P-waves through the sense amplifier 142, the control/timing circuit 128 is able to make a determination as to the rate and regularity of the patient's heart beat. Such information, in turn, allows the control/timing circuit 128 to determine whether the heart 126 of a patient is experiencing an arrhythmia, and to apply appropriate stimulation therapy.

The control/timing circuit 128 further has a memory circuit 144 coupled thereto wherein the patient's historical data, and the operating parameters used by the control/timing circuit 128 are stored. Such operating parameters define, for example, the amplitude of each shock energy pulse to be delivered to the patient's heart 126 within each tier of therapy, as well as the duration of these shock pulses. The memory 144 may take many forms, and may be subdivided into as many different memory blocks or sections (addresses) as needed to store desired data and control information. In some embodiments, the ICD device 125 has the ability to sense and store a relatively large amount of data as a data record, which data record may then be used to guide the operation of the device, i.e., the present operating mode of the device may be dependant, at least in part, on past performance data.

Advantageously, the operating parameters of the implantable device 125 may be non-invasively programmed into the memory 144 through telemetry transmitter 12, in telecommunicative contact with the external programmer or receiver 14 by way of the coupling coil 22. The coil 22 may serve as an antenna for establishing a radio frequency (RF) telemetry link 16 with the receiver 14. The coil 22 may serve as a means for inductively coupling data between the transmitter 12 and the receiver 14. Reference is made to U.S. Pat. No. 4,809,697 (Causey, III et al.) and U.S. Pat. No. 4,944,299 (Silvian) that are incorporated herein by reference. Further, the transmitter 12 allows status information relating to the operation of the ICD device 125, as contained in the control/timing circuit 128 or memory 144, to be sent to the receiver 14 through the telemetry link 16.

The control/timing circuit 128 includes appropriate processing and logic circuits for analyzing the output of the sense amplifier 142 and for determining if such signals indicate the presence of an arrhythmia. Typically, the control/timing circuit 128 is based on a microprocessor, or similar processing circuit, which includes the ability to process or monitor input signals (data) in a prescribed manner, e.g., as controlled by program code stored in a designated area or block of the memory 144.

FIG. 10 is a block diagram of the circuitry needed for the dual-chamber pacemaker 127. The pacemaker 127 is coupled to the patient's heart 126 by way of leads 274 and 276, the lead 274 having an electrode 275 that is in contact with one of the atria of the heart 126, and the lead 276 having an electrode 277 that is in contact with one of the ventricles of the heart 126. The leads 274 and 276 are electrically and physically connected to the pacemaker 127 through a connector 273 that forms an integral part of the housing wherein the circuits of the pacemaker 127 are housed. The connector 273 is electrically connected to a protection network 279, which network 279 electrically protects the circuits within the pacemaker 127 from excessive shocks or voltages that could appear on the electrodes 275 and/or 277 in the event such electrodes were to come in contact with a high voltage signal, e.g., from a defibrillation shock.

The leads 274 and 276 carry stimulating pulses to the electrodes 275 and 277 from an atrial pulse generator (A-PG) 278 and a ventricular pulse generator (V-PG) 280, respectively. Further, electrical signals from the atria are carried from the electrode 275, through the lead 274, to the input terminal of an atrial channel sense amplifier (P-AMP) 282; and electrical signals from the ventricles are carried from the electrode 277, through the lead 276, to the input terminal of a ventricular channel sense amplifier (R-AMP) 284. Similarly, electrical signals from both the atria and ventricles are applied to the inputs of an intracardiac electrogram (IEGM) amplifier 285. The amplifier 285 is typically configured to detect an evoked response from the heart 126 in response to an applied stimulus, thereby aiding in the detection of "capture". Capture occurs when an electrical stimulus applied to the heart is of sufficient energy to depolarize the cardiac tissue, thereby causing the heart muscle to contract, or in other words, causing the heart to beat. Capture does not occur when an electrical stimulus applied to the heart is of insufficient energy to depolarize the cardiac tissue. The dual-chamber pacemaker 127 is controlled by a processor or control system 286, which is comprised of control and timing circuitries that carry out control and timing functions. The control system 286 receives the output signals from the atrial (P-AMP) amplifier 282 over signal line 288. Similarly, the control system 286 receives the output signals from the ventricular (R-AMP) amplifier 284 over signal line 290, and the output signals from the IEGM amplifier 285 over signal line 291. These output signals are generated each time that a P-wave or an R-wave or an evoked response is sensed within the heart 126. The control system 286 also generates trigger signals that are sent to the atrial pulse generator (A-PG) 278 and the ventricular pulse generator (V-PG) 280 over signal lines 292 and 294, respectively. These trigger signals are generated each time that a stimulation pulse is to be generated by the respective pulse generator 278 or 280. The atrial trigger signal is referred to as the "A-trigger", and the ventricular trigger signal is referred to as the "V-trigger".

During the time that either an A-pulse or V-pulse is being delivered to the heart 126, the corresponding amplifier, P-AMP 282 and/or R-AMP 284, is typically disabled by way of a blanking signal presented to these amplifiers from the control system over signal lines 296 and 298, respectively. This blanking action prevents the amplifiers 282 and 284 from becoming saturated from the relatively large stimulation pulses that are present at their input terminals during this time. This blanking action also helps prevent residual electrical signals present in the muscle tissue as a result of the pacemaker stimulation from being interpreted as P-waves or R-waves.

The pacemaker 127 further includes a memory circuit 300 that is coupled to the control system 286 over a suitable data/address bus 302. This memory circuit 300 allows certain control parameters, used by the control system 286 in controlling the operation of the pacemaker, to be programmably stored and modified, as required, in order to customize the pacemaker's operation to suit the needs of a particular patient. Further, data sensed during the operation of the pacemaker may be stored in the memory 300 for later retrieval and analysis.

As with the memory 144 of the ICD device 125 shown in FIG. 9, the memory 300 of the pacemaker 127 (FIG. 10) may take many forms, and may be subdivided into as many different memory blocks or sections (addresses) as needed in order to allow desired data and control information to be stored.

In some embodiments, the pacemaker 127 has the ability to sense and store a relatively large amount of sensed data as a data record, which data record may then be used to guide the operation of the device. That is, the operating mode of the pacemaker 127 may be dependent, at least in part, on past performance data. For example, an average atrial rate may be determined based on the sensed atrial rate over a prescribed period of time. This average rate may then be stored and updated at regular intervals. Such stored rate may then be compared to a present atrial rate and, depending upon the difference, used to control the operating mode of the pacemaker. Other parameters, of course, in addition to (or in lieu of) atrial rate, may be similarly sensed, stored, averaged (or otherwise processed), and then used for comparison purposes against one or more currently-sensed parameters. Modern memory devices allow for the storage of large amounts of data in this manner.

A clock circuit 303 directs an appropriate clock signal(s) to the control system 286, as well as to any other needed circuits throughout the pacemaker 127 (e.g., to the memory 300) by way of clock bus 305.

A telemetry transmitter 12 is further included in the pacemaker 127. The telemetry transmitter 12 is connected to the control system 286 by way of a suitable command/data bus 306. In turn, the telemetry transmitter 12, which is included within the implantable pacemaker 127, may be selectively coupled to an external programming device or programmer or receiver 14 by means of an appropriate telemetry link 16, which telemetry link 16 may be any suitable electromagnetic link, such as an RF (radio frequency) channel, a magnetic link, an inductive link, an optical link, and the like. Through the receiver 14 and the telemetry link 16, desired commands may be sent to the control system 286. Similarly, through this telemetry link 16 with the receiver 14, data commands (either held within the control system 286, as in a data latch, or stored within the memory 300) may be remotely received from the receiver 14. Similarly, data initially sensed through the leads 274 or 276, and processed by the microprocessor control circuits 286, or other data measured within or by the pacemaker 127, may be stored and uploaded to the receiver 14. In this manner, non-invasive communications can be established with the implanted pacemaker 127 from a remote, non-implanted, location.

The pacemaker 127 additionally includes a battery 293 which provides operating power to all of the circuits of the pacemaker 127 via a POWER signal line 295.

It is noted that the pacemaker 127 is referred to as a dual-chamber pacemaker because it interfaces with both the atria and the ventricles of the heart 126. Those portions of the pacemaker 127 that interface with the atria, e.g., the lead 274, the P-wave sense amplifier (or detection circuit) 282, the A-PG 278, and corresponding portions of the control system 286, are commonly referred to as the "atrial channel". Similarly, those portions of the pacemaker 127 that interface with the ventricles, e.g., the lead 276, the R-wave sense amplifier (or detection circuit) 284, the V-pulse generator 280, and corresponding portions of the control system 286, are commonly referred to as the "ventricular channel".

As needed for certain applications, the pacemaker 127 may further include at least one sensor 312 that is connected to the control system 286 of the pacemaker 127 over a suitable connection line 314. While this sensor 312 is illustrated as being included within the pacemaker 127, it is to be understood that the sensor may also be external to the pacemaker 127, yet still be implanted within or carried by the patient. A common type of sensor is an activity sensor, such as a piezoelectric crystal, that is mounted to the case of the pacemaker. Other types of sensors are also known, such as sensors that sense the oxygen content of blood, respiration rate, pH of blood, body motion, and the like. The type of sensor used is not critical to the present invention. Any sensor or combination of sensors capable of sensing a physiological or physical parameter relatable to the rate at which the heart should be beating (i.e., relatable to the metabolic need of the patient), and/or relatable to whether a tachyarrhythmia is likely to soon occur, can be used. Such sensors are commonly used with "rate-responsive" pacemakers in order to adjust the rate (pacing cycle) of the pacemaker in a manner that tracks the physiological or metabolic needs of the patient.

The pacemaker 127 further includes magnet detection circuitry 287, coupled to the control system 286 over signal line 289. It is the purpose of the magnet detection circuitry 287 to detect when a magnet is placed over the pacemaker 127, which magnet may be used by a physician or other medical personnel to perform various reset functions of the pacemaker 127, and/or to signal the control system 286 that an receiver 14 is in place to receive data from, or send data to, the pacemaker memory 300 or control system 286 through the transmitter 12.

The control system 286 may be realized using a variety of different techniques and/or circuits. A preferred type of control system 2286 is a microprocessor-based control system. It is noted, however, that the control system 286 could also be realized using a state machine. Indeed, any type of control circuit or system could be employed for the control system 286.

Representative of the types of control systems that may be used with the invention is the microprocessor-based control system described in U.S. Pat. No. 4,940,052, entitled "Microprocessor Controlled Rate-Responsive Pacemaker Having Automatic Rate Response Threshold Adjustment". Reference is also made to U.S. Pat. Nos. 4,712,555 and 4,944,298, wherein a state-machine type of operation for a pacemaker is described; and U.S. Pat. No. 4,788,980, wherein the various timing intervals used within the pacemaker and their inter-relationship are more thoroughly described. These patents are incorporated herein by reference.

While certain preferred embodiments of the invention have been described, these embodiments have been presented by way of example only, and are not intended to limit the scope of the present invention.

What is claimed is:

1. An implantable device for transmitting binary data to a receiver, comprising:
   a transmitter housed at least in part within a housing;
   the transmitter encoding, modulating, and transmitting the binary data to the receiver over a telemetry link;
   the telemetry link including a housing section that introduces a low pass filtering function as part of the binary data encoding to implement a partial response signaling link.

2. The implantable device as recited in claim 1, wherein the housing includes a titanium can.

3. The implantable device as recited in claim 1, wherein the partial response signaling function employed by the transmitter, includes a $(1-D^2)$ function, where 'D' is a delay operator that represents one bit time.

4. The implantable device as recited in claim 3, wherein the $(1-D^2)$ function is obtained by multiplying an input data signal by a $(1-D)$ function and a $(1+D)$ function in succession.

5. The implantable device as recited in claim 4, wherein the transmitter includes a modulator; and
   wherein the $(1-D)$ function is provided by the modulator.

6. The implantable device as recited in claim 5, wherein the $(1+D)$ function is provided by the housing section.

7. The implantable device as recited in claim 6, wherein the transmitter includes a transmit coil.

8. The implantable device as recited in claim 6, wherein the binary data signal is provided in a Non-Return-to-Zero (NRZ) format.

9. The implantable device as recited in claim 6, wherein the transmitter includes an encoder; and
   wherein the encoder divides the binary data by $(1-D^2)$.

10. The implantable device as recited in claim 6, wherein the transmitter operates in a high data rate mode and in a low data rate mode.

11. A telemetry system for transmitting binary data, comprising:
    a transmitter housed at least in part within a housing;
    the transmitter encoding, modulating, and transmitting the binary data to a receiver over a telemetry link;
    the telemetry link including a housing section that introduces a low pass filtering function for encoding the binary data; and
    the transmitter employing a partial response signaling function which is combined with the low pass filtering function of the housing section, to implement a telemetry link.

12. The telemetry system as recited in claim 11, wherein the housing includes a titanium can.

13. The telemetry system as recited in claim 11, wherein the partial response signaling function employed by the transmitter, includes a $(1-D^2)$ function, where 'D' is a delay operator that represents one bit time.

14. The telemetry system as recited in claim 13, wherein the $(1-D^2)$ function is obtained by multiplying an input data signal by a $(1-D)$ function and a $(1+D)$ function in succession.

15. The telemetry system as recited in claim 14, wherein the transmitter includes a modulator; and
    wherein the $(1-D)$ function is provided by the modulator.

16. The telemetry system as recited in claim 15, wherein the $(1+D)$ function is provided by the housing section.

17. The telemetry system as recited in claim 16, wherein the transmitter includes a transmit coil;
    wherein the binary data signal is provided in a Non-Return-to-Zero (NRZ) format;
    wherein the transmitter includes an encoder; and
    wherein the encoder divides the binary data by $(1-D^2)$.

18. A method for transmitting binary data from a transmitter housing at least in part within a housing, to a receiver, the method comprising:
    encoding, modulating, and transmitting the binary data to the receiver over a telemetry link;
    using the housing, introducing a low pass filtering function for encoding the binary data; and employing a partial response signaling function which is combined with the low pass filtering function of the housing, to implement a telemetry link.

19. The method as recited in claim 18, wherein using the housing includes using a titanium can.

20. The method as recited in claim 18, wherein employing the partial response signaling function by the transmitter, includes employing a $(1-D^2)$ function, where 'D' is a delay operator that represents one bit time.

21. The method as recited in claim 20, wherein employing the $(1-D^2)$ function includes multiplying an input data signal by a $(1-D)$ function and a $(1+D)$ function in succession.

22. The method as recited in claim 21, wherein a modulator provides the $(1-D)$ function;
wherein the housing provides the $(1+D)$ function.

23. The method as recited in claim 22, further including dividing the binary data by $(1-D^2)$.

\* \* \* \* \*